(12) United States Patent
Kadobayashi (10) Patent No.: US 8,221,128 B2
(45) Date of Patent: Jul. 17, 2012

(54) TOOTH FOR TOOTH MODEL, COMPRISING ENAMEL PORTION IMPREGNATED WITH RESIN OR LOW MELTING POINT GLASS, AND METHOD FOR PRODUCING THE SAME

(75) Inventor: Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 598 days.

(21) Appl. No.: 12/219,426

(22) Filed: Jul. 22, 2008

(65) Prior Publication Data

US 2009/0035738 A1 Feb. 5, 2009

(30) Foreign Application Priority Data

Aug. 1, 2007 (JP) .................................. 2007-200403
May 16, 2008 (JP) .................................. 2008-129872

(51) Int. Cl.
*G09B 23/28* (2006.01)
(52) U.S. Cl. .......................................... 434/263; 264/19
(58) Field of Classification Search .................. 434/263, 434/264; 264/16, 19
See application file for complete search history.

(56) References Cited

U.S. PATENT DOCUMENTS

| | | | | |
|---|---|---|---|---|
| 2,750,670 A * | 6/1956 | Vigg | ............................. | 434/264 |
| 4,772,436 A * | 9/1988 | Tyszblat | ........................ | 264/19 |
| 4,902,232 A * | 2/1990 | Neustadter | .................... | 434/263 |
| 5,776,382 A * | 7/1998 | Kim et al. | ........................ | 264/16 |
| 6,524,105 B2 * | 2/2003 | Raffeiner | ........................ | 433/213 |
| 6,988,894 B2 * | 1/2006 | Lee et al. | ........................ | 434/263 |
| 7,600,398 B2 * | 10/2009 | Salomonson et al. | ........ | 65/59.21 |
| 2006/0024652 A1 * | 2/2006 | Ose et al. | ........................ | 434/263 |
| 2006/0191916 A1 | 8/2006 | Stephan et al. | | |

FOREIGN PATENT DOCUMENTS

JP 2007-323052 12/2007
WO 2008/063620 5/2008

OTHER PUBLICATIONS

European Search Report (in English language) issued Dec. 9, 2009 in corresponding European Patent Application No. 08 01 3433.

* cited by examiner

*Primary Examiner* — Gene Kim
*Assistant Examiner* — Joseph B Baldori
(74) *Attorney, Agent, or Firm* — Wenderoth, Lind & Ponack, LLP (57) ABSTRACT

An object of the present invention is to provide a tooth model capable of exhibiting grinding feel similar to that of a natural tooth, with which students aspiring to become dentists experience intraoral work and perform training related to a treatment, and also experience formation of an abutment tooth, formation of cavity or the like. A difference in the grinding feel between tooth enamel and dentin, which constitute a natural tooth, is reproduced by impregnating a sintered body formed integrally of an inorganic powder such as alumina with a thermosetting resin or a low melting point glass to form an enamel portion.

12 Claims, 5 Drawing Sheets

TOOTH FOR TOOTH MODEL, COMPRISING ENAMEL PORTION IMPREGNATED WITH RESIN OR LOW MELTING POINT GLASS, AND METHOD FOR PRODUCING THE SAME

BACKGROUND OF THE INVENTION

1. Field of the Invention

The present invention relates to a tooth used for a jaw and tooth model, using which students aspiring to become dentists can experience intraoral work and perform training related to treatment. A tooth for a jaw and tooth model is a tooth which is used for simulation of an intraoral remedial procedure or training related to treatment using a jaw and tooth model in a university. More particularly, the present invention relates to a tooth which is used to experience formation of an abutment tooth, formation of cavity or the like by grinding the tooth, and a method for producing the same.

2. Description of the Related Art

In training related to dental treatment, teeth extracted from human bodies and animals have conventionally been used so as to experience the grinding feel of a natural tooth. However, there are hygienic problems associated with extracted teeth and infection may occur if hygiene control is not sufficiently conducted. Thus it was impossible to conduct training freely. Furthermore since extracted teeth comprise a natural living material, there arises a problem of corruption and it is necessary to pay a careful attention to storage.

Therefore, there has been a need for a method which enables the experience of grinding feel of a tooth without using a natural tooth.

Now a tooth for a jaw and tooth model, which is used for training related to intraoral treatment, is often produced using an epoxy resin or a melamine resin, and are well known in the art.

However, a tooth for a jaw and tooth model formed of an epoxy resin or a melamine resin is in the form of a natural tooth, but exhibits grinding feel which is different from that of a natural tooth. Therefore, even when performing training related to the formation of an abutment tooth and formation of cavity, grinding feel and working properties are different from those of actual intraoral work, and thus the training effect could not be obtained.

Specifically, a natural tooth comprises tooth enamel and dentin, and tooth enamel and dentin are harder than resin, whereas, epoxy resin and melamine resin are soft. Thus there is a tendency to over grind and even when performing training using such a model tooth, the grinding may not be similar to that of a hard natural tooth.

Furthermore, tooth enamel and dentin, with which a crown portion of dentin is coated, have different hardnesses. As a result, in case of a transition during grinding from tooth enamel to dentin, the dentin may be excessively ground and thus a tooth may not be satisfactorily produced.

As a result of the need for a harder material, a composite type tooth is commercially available. However even in case of a composite type tooth, since the dentin portion and the enamel portion exhibit the same grinding feel, the grinding feel of the tooth is different from that of a natural tooth. Therefore, even when performing training related to the formation of an abutment tooth and the formation of a cavity, the grinding feel and working properties are different from those in case of intraoral work in practice, and thus the training effect could not be obtained. To state the matter clearly, the grinding feel includes a sliding sensation and is substantially different from a natural tooth.

That is, it is required that the grinding feel varies similarly to a natural tooth in the transition portion from the enamel portion to the dentin portion of a tooth for a jaw and tooth model. Therefore a mater of course, it is important that the enamel portion reproduces a grinding feel of tooth enamel, while the dentin portion reproduces a grinding feel of dentin.

Japanese Unexamined Utility Model Publication (Kokai) 1-90068 discloses that a tooth enamel layer is formed of glass/ceramics having a Vickers hardness controlled within a range from 350 to 450, comprising a phlogopite crystal $[NaMg_3(Si_3AlO_{10})F_2]$ and a lithia-alumina-silica-based crystal $(Li_2O.Al_2O_3.2SiO_2, Li_2O.Al_2O_3.4SiO_2)$ precipitated simultaneously; a tooth root layer is prepared in advance by adding white, red and yellow colorants to a polyol (base resin), mixing with an isocyanate prepolymer (curing agent), injecting the mixture into a silicone rubber mother mold under vacuum conditions and curing the mixture at a normal temperature; and a dentin recognition layer, which exists between the tooth enamel layer and the tooth root layer thereby bonding both layers, and is formed of an adhesive resin having an opaque color.

However, the tooth comprising a tooth enamel layer formed of a phlogopite crystal or a lithia-alumina-silica-based crystal is not well adapted for use because it feels too hard when grinding as compared with a natural tooth, and also it is not well adapted for use because the dentin recognition layer is formed of an adhesive resin which feels too soft when grinding.

Furthermore, dentin layer is formed of an adhesive layer is disclosed. It is described that an enamel layer portion and a tooth root layer portion are formed and bonded. It is recognized as the dentin layer formed of a thick adhesive layer.

Japanese Unexamined Patent Publication (Kokai) No. (hereinafter referred to briefly as "JP-A-") 5-224591 discloses a tooth model which has grinding properties extremely similar to those of a natural tooth, and is suited for the training of practical dental grinding.

The tooth model comprises a crown portion whose surface has a Knoop hardness of at least 70 or more and a tooth root portion whose surface has a Knoop hardness of at least 10 to 40. The tooth model contains, as main components, an inorganic matter powder and a crosslinking resin in a weight ratio of 20%:80% to 70%: 30%.

The above prior art discloses that "a tooth model may be formed of a raw material having any hardness, for example, metal, ceramics or a resin, or may be a cavity in view of the method for producing a tooth model and economic considerations". However, this is not a tooth model which can exhibit a difference in grinding properties between the enamel portion and the dentin portion.

JP-A-5-216395 discloses a tooth model which has grinding properties extremely similar to those of a natural tooth and is suited for the training of practical dental grinding, and a method for producing the same. The tooth model contains, as main components, a hydroxyapatite powder having a porosity of 40 to 80% and a (meth)acrylate ester-based resin in a weight ratio of 20%: 80% to 50%: 50%. However, this is not a tooth model which can exhibit a difference in grinding properties between the enamel portion and the dentin portion.

JP-A-5-241498, JP-A-5-241499 and JP-A-5-241500 describe an inorganic filler and a hydroxyapatite filler. However, in all tooth models disclosed in these publications, a resin is used as a base material and thus the problem of the grinding feel is not solved. They are not tooth models which can exhibit a difference in grinding properties between the enamel portion and the dentin portion.

JP-A-2004-94049 describes an invention which provides a model tooth for dental training, which enables an accurate shape measurement with laser beam.

The specification discloses that "known materials can be used as a material constituting a surface of a crown portion of the model tooth of the present invention and there can be used porcelain materials such as ceramics; thermoplastic resin materials such as acryl, polystyrene, polycarbonate, an acrylonitrile-styrene-butadiene copolymer (ABS), polypropylene, polyethylene, and polyester; thermosetting resin materials such as melamine, urea, unsaturated polyester, phenol, and epoxy; and materials obtained by adding various organic and inorganic reinforcing fibers (for example, glass fiber, carbon fiber, pulp, synthetic resin fiber, etc.), various fillers (for example, talc, silica, mica, calcium carbonate, barium sulfate, alumina, etc.), colorants (for example, pigment, dye, etc.) and various additives (for example, weathering agents, antistatic agents, etc.) to these main raw materials". However, there is no description about preferable materials, and thus the problem of grinding feel is not solved.

As a result of a study, the present inventors have found that it is necessary to use a sintered body of an inorganic material so as to exhibit the grinding feel of a natural tooth. Because of the difficulty in controlling a hardness of an inorganic material, it is difficult to form an enamel portion and a dentin portion while controlling the hardness.

In particular, when the enamel portion and the dentin portion of the tooth model are formed of a sintered body of the same inorganic material, it was difficult to reproduce a difference in the grinding feel between the enamel portion and the dentin portion.

It is proposed that the enamel portion and the dentin portion are separately formed and a grinding feel of each portion is adjusted so as to reproduce a difference in grinding feel between the enamel portion and the dentin portion.

It is necessary to unify the density, particle shape and firing temperature of the sintered body so as to adjust the grinding feel of the sintered body. The difference in a shrinkage rate and a thermal expansion coefficient between the enamel portion and the dentin portion upon firing results in breaking, peeling and cracking. In addition, a gap may be formed between the dentin portion and the enamel portion. Thus, chipping may occur upon grinding and the gap gives a feel different from the grinding feel of a natural tooth. Thus the resultant tooth was not well adapted for use.

In particular, when the enamel portion and the dentin portion are formed as separate sintered bodies, adhesion between the enamel portion and the dentin portion is required and grinding feel largely varies in an interfacial region including the adhesion portion. That is, there is obtained a tooth model which causes a strange sensation during the transition from the enamel portion to the dentin portion, and which is very difference from a natural tooth.

When a natural tooth is ground, a unique tough grinding feel upon grinding of a living body is obtained. Although various methods have been studied so as to obtain a tough grinding feel peculiar to a natural tooth, sufficient grinding feel cannot be obtained using resin, composite or the like and such a sensation can not be obtained while pouring water on a conventional tooth for a jaw and tooth model. A grinding feel is required in which users feel a tougher grinding feel than that of an inorganic material even in case of the tooth enamel because of a similar phenomenon.

In view of the above, a conventional tooth model is not satisfactory with respect to grinding properties and, therefore, it is required to develop a tooth model having grinding properties similar to those of a natural tooth. However, the tooth models have not exhibit a sufficient grinding feel. It is particularly required to develop a tooth having toughness peculiar to a natural tooth, and there has never been obtained a tooth model capable of exhibiting a difference in grinding properties between the enamel portion and the dentin portion.

However, neither a specific composition of a tooth model capable of realizing grinding feel of tooth enamel and dentin of a natural tooth, nor a method for producing the same has been studied or reported.

Therefore, it is required to develop a tooth model, the enamel portion and the dentin portion being formed of the same inorganic material, which exhibits a tough grinding feel peculiar to a natural tooth and which also reproduces a difference in grinding feel between the enamel portion and the dentin portion.

A method of reproducing tooth pulp peculiar to a natural tooth has not been developed heretofore, and thus dental students could not experience exposure to tooth pulp. Dental pulp exposure (grinding down the tooth pulp portion) is the most important technique in a dental treatment. In case where tooth pulp exposure was carried out by mistake, the subsequent treatment method must be learned at the same time.

As a dental caries progresses in a natural tooth, the treatment position expands into the enamel layer, the dentin layer and the tooth pulp, and training for a root canal treatment such as a pulpectomy is most important. When a pulpectomy is carried out, since the tooth pulp is removed by a reamer and sensation of rubbing of the dentin wall surface with the reamer completely varies, training related to root canal filling could not be carried out.

In a treatment of tooth pulp, a tooth designed for training of a root canal treatment is used, and also training of a root canal treatment (root canal cleaning, root canal extension, etc.) is carried out using a tooth with a small hole formed of a box-shaped acryl. However, sufficient training cannot be carried out since it is impossible to mount the tooth on a jaw and the hardness of dentin varies.

It is required to develop a tooth for a jaw and tooth model, which enables these experiences. In particular, dental students learn by hand a sensation of whether or not tooth pulp is completely removed upto an apical foramen during root canal cleaning, and thus it is difficult for beginners. Therefore, it is required to perform training using a tooth for a jaw and tooth model in which tooth pulp in a natural tooth is reproduced.

Although removal of dental caries is an important procedure in a dental treatment, a carious dental portion is softer than a usual dentin portion and thus it is difficult to grind the carious dental portion. Therefore, it is necessary to perform training using a tooth for a jaw and tooth model in which dental caries in a natural tooth are reproduced. It is also required to develop a method of confirming that a carious dental portion has been accurately removed.

SUMMARY OF THE INVENTION

An object of the present invention is to provide a tooth for a jaw and tooth model, which enables the experience of a sensation similar to that in treating a natural tooth. Particularly, an object of the present invention is to provide a tooth for a jaw and tooth model in which a difference in a grinding feel between tooth enamel and dentin of a natural tooth is reproduced in a tooth for a jaw and tooth model, comprising an enamel portion and a dentin portion.

The present invention provides a tooth for a jaw and tooth model, which is used for training related to a treatment, comprising an enamel portion and a dentin portion, wherein the enamel portion and the dentin portion are formed of a sintered body of an inorganic powder, voids exist between particles of the inorganic powder, which constitutes the sintered body, and the voids in the enamel portion are impregnated with a resin or a low melting point glass.

In the tooth for a jaw and tooth model of the present invention, the enamel portion and the dentin portion can be integrally formed of a sintered body of an inorganic powder. The enamel portion is formed by impregnating a part of the resultant sintered body with a resin or a low melting point glass.

In the tooth for a jaw and tooth model of the present invention, a thermosetting resin such as a urea resin, a melamine resin, a phenol resin or an epoxy resin, or a thermoplastic resin containing a crosslinking agent can be used as the resin, and a glass capable of flowing at 200 to 600° C. can be used as the low melting point glass.

Since the enamel portion and the dentin portion are integrally formed of a sintered body with the same composition, an adhesive layer of the enamel portion and the dentin portion is eliminated. As a result, a transition from the enamel portion to the dentin portion upon grinding is smoothly conducted.

A powder of inorganic materials such as alumina, zirconia, titanium oxide and silica can be used for the tooth for a jaw and tooth model of the present invention, but is not limited thereto, and various inorganic powders and a mixture thereof can be used.

A tooth for a jaw and tooth model is a substitute for a hardest natural tooth in a human body and a tooth formed from a conventional material exhibits a soft feel upon grinding, whereas, the tooth for a jaw and tooth model according to the present invention is formed of an inorganic material and therefore a grinding feel similar to that of a natural tooth can be obtained. It is possible to experience a grinding feel similar to that when using an intraoral diamond grinding material (using an air turbine) rotating at a high speed of 400,000 rpm.

In the present invention, it is preferred that an inorganic powder is injection-molded using a ceramic injection molding (CIM) technique to form an injection molding having a desired shape and the resultant injection molding is fired.

Since the injection molding is contacted with a grinding material rotating at a high speed and therefore adaptability between the tooth and the jaw is important, a CIM technique capable of accurately forming is preferably used.

The shape of a dental crown of the tooth model is also important and it is important to serve as a target of formation of an abutment tooth and formation of a cavity and to accurately express a raised portion, fossa and cusp, and thus molding using a CIM technique is suitable.

In the tooth for a jaw and tooth model of the present invention, a tooth pulp portion can be formed in the dentin portion. The tooth pulp portion is filled with a resin, a silicone rubber, a wax or a water-soluble material.

In the tooth for a jaw and tooth model of the present invention, a false carious dental portion can be formed between the enamel portion and the dentin portion, or at the periphery thereof. The false carious dental portion is formed of a resin or a sintered body of an inorganic powder.

The tooth for a jaw and tooth model of the present invention is a sintered body integrally molded by using an inorganic material, and includes an enamel portion and a dentin portion. Since the tooth is integrally molded, an adhesive layer does not exist between the enamel portion and the dentin portion and thus a transition upon grinding can be smoothly conducted without experiencing the soft feel of an adhesive.

Since the enamel portion is formed by impregnating with a thermosetting resin, a thermoplastic resin containing a crosslinking agent, or a low melting point glass, a hard grinding feel similar to that of the enamel layer can be obtained as compared with the case when impregnation is not performed.

Since a grinding feel similar to that of a natural tooth is obtained in both of the dentin portion and the enamel portion and a grinding feel transiting from the enamel portion to the dentin portion is similar to that of a natural tooth, training related to grinding a natural tooth can be easily conducted even when using a model.

By forming an abutment tooth and cavity using the tooth for a jaw and tooth model of the present invention, it is possible to quickly experience grinding feel similar to that of natural tooth and to easily experience formation. Such a formation technique can be quickly mastered.

It is also possible to experience a technique of a root canal treatment or dental caries treatment by forming a tooth pulp portion or a false carious dental portion on the tooth of the present invention.

DETAILED DESCRIPTION OF THE INVENTION

Figure 1:
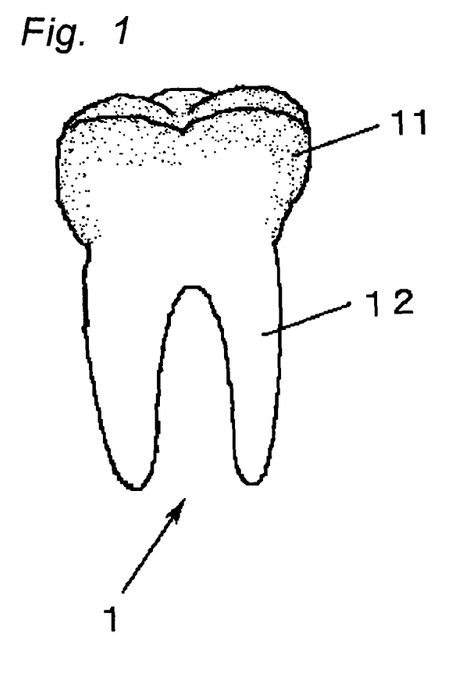
FIG. 1 is a sectional view showing a tooth for a jaw and tooth model of the present invention.

As shown in FIG. 1, the tooth for a jaw and tooth model of the present invention includes at least an enamel portion 11 and a dentin portion 12.

Figure 2:
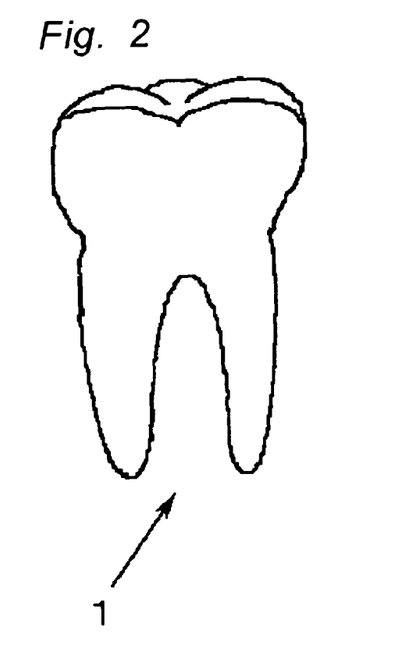
FIG. 2 is a sectional view showing a tooth for a front tooth model before forming an enamel portion.

As shown in FIG. 2, the enamel portion 11 and the dentin portion 12 are integrally formed of a sintered body of an inorganic powder, and a desired region of the sintered body is impregnated with a resin or a low melting point glass to form an enamel portion 11.

Figure 3:
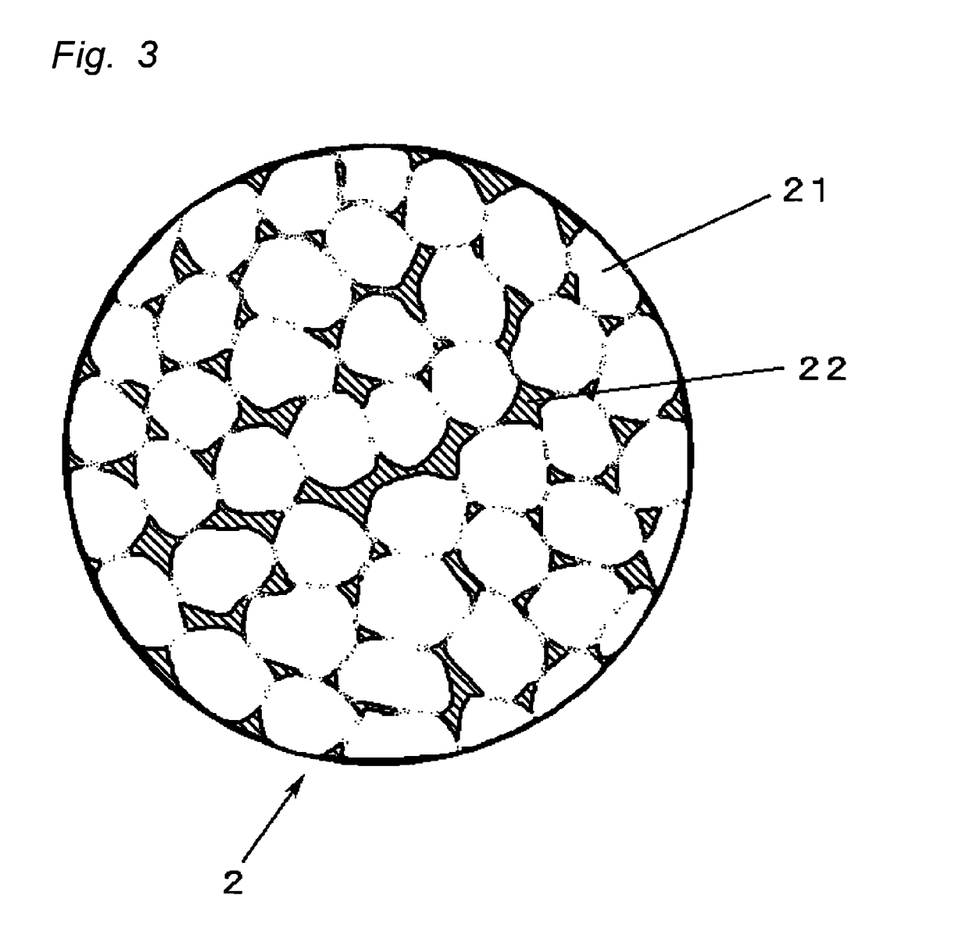
FIG. 3 is an enlarged view showing an inorganic powder sintered body.

The sintered body of an inorganic powder 2, which constitutes the tooth for a jaw and tooth model of the present invention 1, is formed by sintering particles 21 of an inorganic powder as shown in FIG. 3. Furthermore, voids 22 exist between the particles 21.

These voids 22 are impregnated with a resin or a low melting point glass 3 to form an enamel portion 11 which is harder than the dentin portion 12 and also reproduces a tough grinding feel similar to that of a natural tooth.

Figure 4:
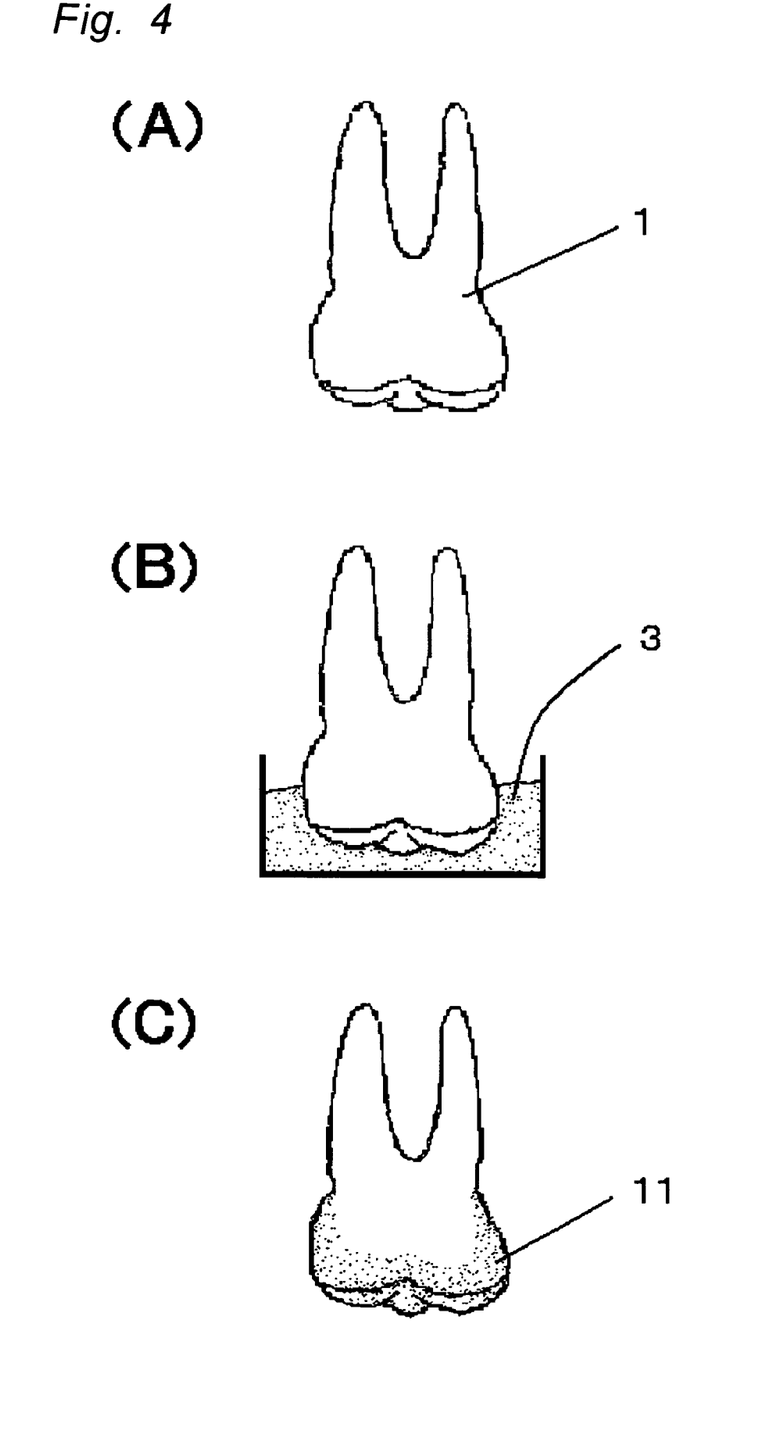
FIG. 4 is a schematic view showing a method for producing a tooth for a jaw and tooth model of the present invention.

As shown in FIG. 4, the inorganic powder is injection-molded to form an injection molding having a desired shape and the resultant injection molding is fired to obtain a sintered body (FIG. 4A), which is then immersed in a vessel filled with a resin or a low melting point glass 3 (FIG. 4B) thereby impregnating a desired portion, which would form the enamel portion 11, with a resin or a low melting point glass (FIG. 4C).

In a vacuum vessel, the sintered body is preferably impregnated with the resin or low melting point glass 3. Impregnation can be easily conducted by extracting the air in the voids 22 of the sintered body 2.

Figure 5:
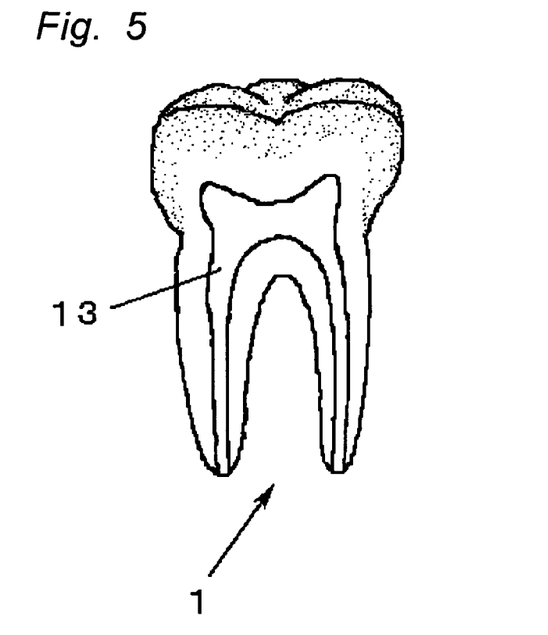
FIG. 5 is a sectional view showing a tooth for a jaw and tooth model, which includes a tooth pulp portion, of the present invention.

In the tooth for a jaw and tooth model of the present invention 1, a tooth pulp portion 13 can be formed in the dentin portion 12 (FIG. 5).

In order to form the tooth pulp portion 13 in the dentin portion 12, a mold having a desired tooth pulp shape is formed using a combustible material such as an epoxy resin. The mold having a tooth pulp shape is set in a die and an injection molding is formed of an inorganic powder. The injection molding is fired thereby burning out the mold having a tooth pulp shape to obtain a tooth 1 including a space having a tooth pulp shape therein. The space of the resultant tooth pulp shape is filled with a resin, a silicone rubber, a wax or a water-soluble material to form the tooth pulp portion 13.

Figure 6:
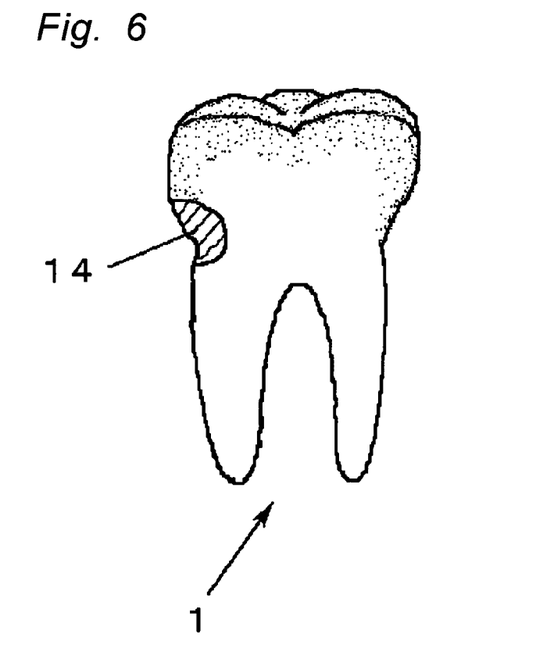
FIG. 6 is a sectional view showing a tooth for a jaw and tooth model, which includes a false carious dental portion, of the present invention.

In the tooth for a jaw and tooth model of the present invention, a false carious dental portion 14 can be formed between the enamel portion 11 and the dentin portion 12, or at the periphery thereof. FIG. 6 is a schematic view in which the false dental caries 14 is formed at a transition portion of the enamel portion 11 and the dentin portion 12 of a tooth for a jaw and tooth model.

Figure 7:
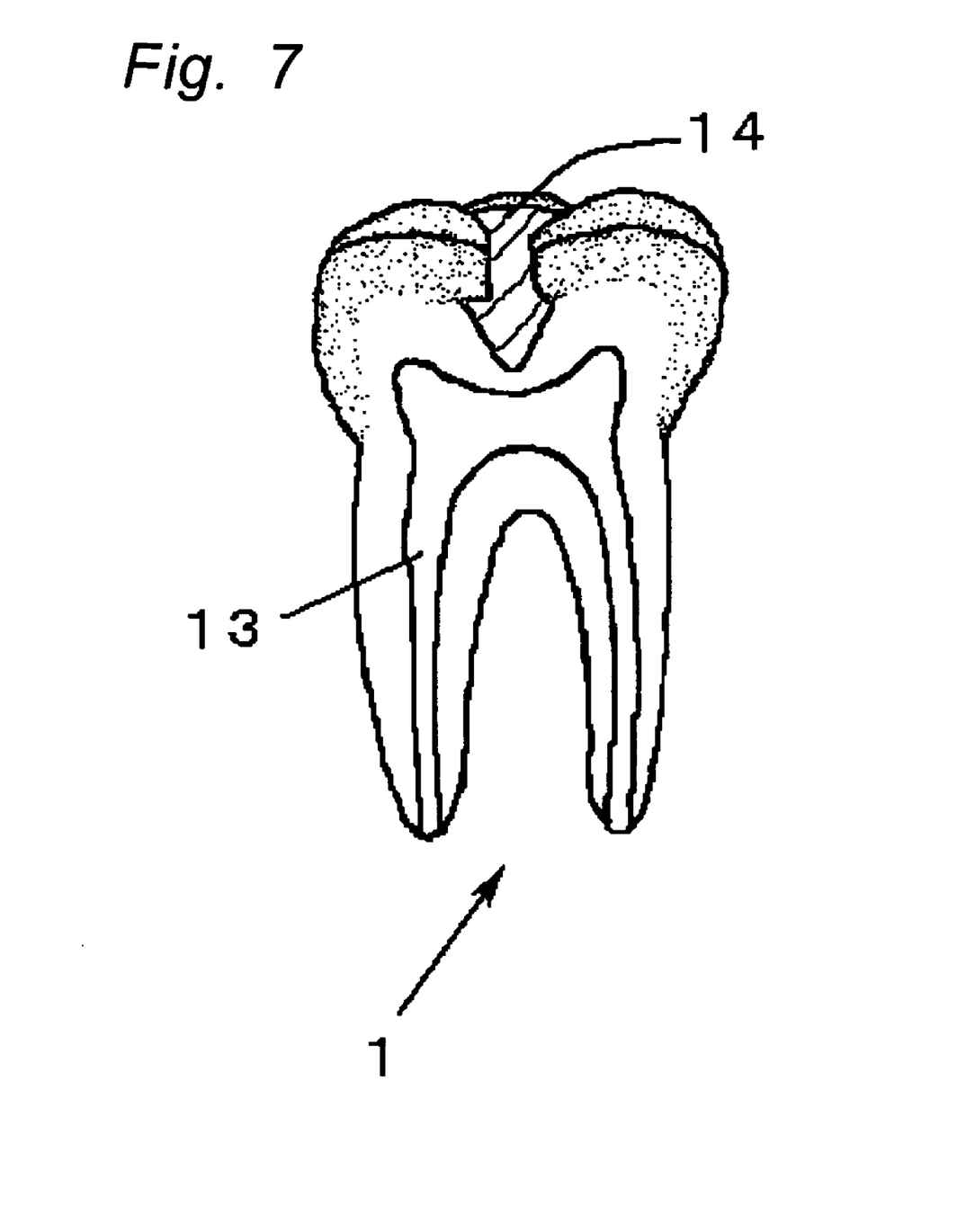
FIG. 7 is a sectional view showing a tooth for a jaw and tooth model, which includes a tooth pulp portion and a false carious dental portion, of the present invention.

As shown in FIG. 7, the false carious dental portion 14 can be formed so as to pierce through the dentin portion from an occlusal surface of the enamel portion, and also the false carious dental portion 14 can be formed together with the tooth pulp portion 13.

The false carious dental portion 14 is formed of a sintered body of an inorganic powder, a resin or a composite. When the false carious dental portion 14 is formed of the resin or composite, it is possible to visually confirm the degree of removal of the carious dental portion by adding a colorant, a fluorescent material or an X-ray contrast medium to the sintered body of an inorganic powder, the resin or composite.

Since the tooth for a jaw and tooth model of the present invention can be colored white, ivory, milky-white or translucent by using an inorganic pigment, like a natural tooth, it is possible to experience more realistic grinding. The color is preferably white, ivory, or milky-white.

In the tooth for a jaw and tooth model of the present invention, a jaw field and a mannequin portion can be appropriately selected. It is important carry out a procedure in order to confirm the suitability of the selection. For example, it is important to appropriately adjust the size of a tooth inserting inlet of a jaw and tooth model.

Examples of the inorganic powder, which can be used to form a tooth for a jaw and tooth model of the present invention, include powders of alumina-based, zirconia-based, silica-based, aluminum nitride and silicon nitride ceramics, or glass. Among these, powders of alumina-based and zirconia-based ceramics are preferred.

The alumina-based or zirconia-based ceramics mean that the content of alumina or zirconia is from 0 to 100%, preferably from 80 to 100%, and more preferably from 95 to 100%, based on the composition of the sintered body. Particularly, the content of alumina is from 50 to 100%, preferably from 70 to 100%, and more preferably from 90 to 100%.

Powders of alumina-based ceramics are preferably used as the organic powder.

When the tooth is formed of a sintered body of an inorganic powder, the hardness is adjusted by a method of increasing a particle size, a method of increasing voids, a method of varying the composition, a method of varying the firing temperature, or a method of varying the retention time.

The average particle diameter of the inorganic powder sintered body is adjusted within a range from 0.1 to 10 μm, and preferably from 1.0 to 5.0 μm.

The firing temperature varies depending on the composition. The firing temperature is from 800 to 1,200° C. when a large amount of a glass component such as silica is contained. In case of alumina, the firing temperature is from 1,200 to 1,600° C., and preferably from 1,400 to 1,550° C.

The tooth for a jaw and tooth model of the present invention is preferably formed of a sintered body of an alumina powder. In this case, the primary particle diameter of the alumina powder is preferably from 0.2 to 5 μm. It is preferred to fire at a firing temperature of 1,300 to 1,600° C.

The firing temperature has a close relation with the grinding feel and it must be adjusted according to the particle size or raw material. Similarly, the retention time at a firing temperature also has a close relation with the grinding feel and it must be adjusted according to the particle size and raw material.

Vickers hardness of the sintered body constituting the tooth for a jaw and tooth model of the present invention is preferably from 300 to 1,000, and more preferably from 300 to 600.

As long as the grinding feel of the alumina sintered body is not impaired, a metal oxide such as silica may be added to the tooth composition.

An injection molding for obtaining a sintered body of the tooth for a jaw and tooth model of the present invention is preferably formed by using a CIM technique which is often used as a method for forming ceramics.

The CIM technique is a technique of forming an inorganic powder and includes the following steps of:
(1) kneading alumina with a binder (which is thermally decomposed at about 1,000° C. or lower) to form pellets;
(2) making a die for an injection molding having a given shape and injection-molding the pellets obtained in the step (1);
(3) removing the binder through degreasing (decomposing a binder component by raising the temperature) after molding; and
(4) firing the degreased injection molding at a predetermined temperature to obtain a desired sintered body.

Examples of the binder, which can be used in the present invention, include stearic acid, polyvinyl alcohol, a thermoplastic resin and wax. Stearic acid or polyvinyl alcohol is preferably used.

The thermoplastic resin means a resin which can obtain sufficient thermoplasticity for the purposes of molding by applying heat.

Specific examples of a thermoplastic resin, which can be used in the present invention, include acryl-based, styrene-based, olefin-based, vinyl chloride-based, urethane-based, polyamide-based, polybutadiene-based, polyacetal-based, unsaturated polyester-based, polycarbonate and polyphenylene ether resins.

Polysulfone-based, polyimide, polyether imide and polyether ether ketone resins can also be appropriately used. Among these resins, an acryl-based resin is particularly preferred.

Both natural wax and synthetic wax can be used as a wax. Typical examples of the natural wax include animal/vegetable wax, mineral wax and petroleum wax. As a synthetic wax, blended wax and polyethylene wax can be used, and paraffin wax is preferred. Fats and oils are also included in the wax. Fats and oils mean a glycerin ester of fatty acid, are insoluble in water and soluble in an alcohol. Fats and oils are preferably in the form of solid fat at a normal temperature (37° C., atmospheric pressure) and examples thereof include vegetable Japan tallow, animal beef tallow- and lard. Specifically, lauric acid, myristic acid, palmitic acid, behenic acid, stearic acid, and fats and oils extracted from a living body can be used, and fats and oils extracted from a living body are preferred. Among these, fats and oils extracted from a living body (for example, lard, tallow, etc.) are particularly preferred.

A tooth of a sintered body obtained by injection molding using a CIM technique, followed by the steps of degreasing and firing is immersed in a resin or a molten low melting point glass thereby impregnating a desired portion with the resin or glass to form an enamel portion. It is preferred that the tooth of the sintered body is impregnated with the resin or molten glass under reduced pressure and then the pressure is returned to a normal pressure.

A thermosetting resin and a thermoplastic resin can be used as the impregnating resin in the present invention.

A thermosetting resin is better than a thermoplastic resin. A thermosetting resin means a resin which is not dissolved in a solvent after processing and is not softened even when heated again. A urea resin, a melamine resin, a phenol resin and an epoxy resin can be typically used, and a melamine resin and an epoxy resin are preferred. Among these, an epoxy resin is most preferred.

The thermosetting resin is preferably a chemical polymerizable resin because the voids portion of the sintered body is impregnated with the resin and the resin can be easily cured.

The chemical polymerizable resin means a resin which is polymerizable using a chemical catalyst even when it is originally included in the thermosetting resin or thermoplastic resin. A chemical polymerizable resin, which contains a crosslinking agent and has no thermoplasticity, is particularly preferred.

The thermoplastic resin means a resin which can obtain sufficient thermoplasticity for the purposes of molding by applying heat.

Specific examples of a thermoplastic resin, which can be used to form the enamel portion in the present invention, include acryl-based, styrene-based, olefin-based, vinyl chloride-based, urethane-based, polyamide-based, polybutadiene-based, polyacetal-based, saturated polyester-based, polycarbonate, and polyphenylene ether resins. Among these resins, acryl-based, styrene-based, urethane-based and polyamide-based resins are particularly preferred.

A preferred aspect with respect to the thermosetting resin can be obtained by mixing the thermoplastic resin with a crosslinking agent. That is, it is possible to perform training of tooth grinding without the resin being dissolved by heat generated upon grinding.

The glass which can be used to form the enamel portion of the present invention is not specifically limited, and is preferably a low melting point glass which flows at a temperature within a range from 200 to 600° C. The temperature at which the glass begins to flow is preferably 600° C. or lower because the sintered body formed of an inorganic powder is not deformed.

The low melting point glass is preferably an alumina silicate glass. A preferable glass has the composition consisting of 5 to 40% of $Al_2O_3$ and 20 to 90% of $SiO_2$, more preferably 20 to 35% of $Al_2O_3$ and 35 to 70% of $SiO_2$, and still more preferably 25 to 33% of $Al_2O_3$ and 50 to 65% of $SiO_2$.

In order to lower the melting point, it is preferred that the glass contains 1 to 15%, and preferably 3 to 10% of at least one of sodium oxide, potassium oxide, lithium oxide and lanthanoid oxide. It is particularly preferred to add 2 to 10% of $LaO_2$.

It is preferred to appropriately add other components such as boric acid, phosphoric acid, sodium oxide, potassium oxide, lithium oxide, lime, magnesia, strontium oxide, barium oxide, lead oxide, titania, zinc oxide, and zirconia.

It is preferred to appropriately add additives such as burnt ocher, cobalt trioxide, nickel oxide, potassium dichromate, chromium oxide, manganese dioxide, potassium permanganate, vanadium pentoxide, metallic selenium, sodium selenite, cupric oxide, copper sulfate, cuprous oxide, gold chloride, silver nitrate, sublimed sulfur, sodium sulfide, fluorite, sodium fluorosilicate, and apatite.

It is possible to only color an enamel portion by adding components having a coloring effect to a glass so as to enhance the visibility of the enamel portion.

In order to reproduce the same tough grinding feel as that of a natural tooth, voids of the portion of the sintered body, which would form the dentin portion of the tooth for a jaw and tooth model of the present invention, can be impregnated with a water-soluble material, a thermosoluble material or an organic material after forming the enamel portion.

Any water-soluble material can be used without any limitation as long as it is a water-soluble polymer with which voids of the sintered body can be impregnated. At least one of a polysaccharide or a protein is preferably used. Among these, a protein is preferred.

When impregnated with the water-soluble material, the effect is exerted by water pouring or previously impregnating water.

Dextrin, glycogen, cellulose, pectin, konjak mannan and glucomannan, and alginic acid are preferably used as polysaccharides. Among these, cellulose, pectin, konjak mannan and glucomannan are preferred because a certain viscosity is required.

The protein may be a polymer compound consisting mainly of a polypeptide comprising about twenty kinds of L-α-amino acids. In view of the composition, a simple protein consisting only of amino acid and a conjugated protein containing nucleic acid, phosphoric acid, lipid, saccharide and metal are preferably used. Gelatin, an agar-based material, collagen and elastin are more preferred. Gelatin and an agar-based material are still more preferred because not only these materials easily dissolve in water, but also the shape must be retained at the voids portion of the sintered body.

A wax-based material can be used as the thermosoluble material.

When impregnated with the thermosoluble material, the effect is exerted by dissolving through frictional heat generated upon grinding. The wax exerts an effect similar to that of polysaccharides or protein without using water, and it is possible to easily perform training of tooth grinding without using a water pouring equipment.

As a wax, both natural wax and synthetic wax can be used. Typical examples of natural waxes include animal/vegetable wax, mineral wax and petroleum wax. As synthetic wax, blended wax and polyethylene wax can be used, and paraffin wax is preferred. Fats and oils are also included in the wax. Fats and oils mean a glycerin ester of fatty acid and are insoluble in water and soluble in an alcohol. Fats and oils are preferably in the form of solid fat at a normal temperature (37° C., atmospheric pressure) and examples thereof include vegetable Japan tallow, animal beef tallow and lard. Specifically, lauric acid, myristic acid, palmitic acid, behenic acid, stearic acid, and fats and oils extracted from a living body can be used, and fats and oils extracted from a living body are preferred. Among these, fats and oils extracted from a living body (for example, lard, tallow, etc.) are particularly preferred.

It is possible to help impregnation by mixing a surfactant upon impregnation. That is, an auxiliary of the surfactant plays an important role so as to impregnate a voids portion of a sintered body with a water-soluble material or a thermosoluble material.

The surfactant can also be used as a water-soluble material.

Anionic, nonionic, cationic and amphoteric surfactants can be appropriately used. Among these surfactants, anionic and nonionic surfactants are preferred. As the anionic surfactant, a fatty acid salt (soap) $C_{11}H_{23}COONa$, an alpha-sulfo fatty acid ester salt (α-SFE) $C_{10}H_{21}$—$CH(SO_{33}Na)COOCH_3$, an alkyl benzene sulfonate (ABS) $C_{12}H_{25}$—$(C_6H_4)SO_3Na$, an alkyl sulfate (AS) [higher alcohol-based] $C_{12}H_{25}$—$OSO_3Na$, an alkyl ether sulfate ester salt (AES) $C_{12}H_{25}$—$O(CH_2CH_2O)_3SO_3Na$, and a triethanolamine alkyl sulfate $C_{12}H_{25}$—$OS^-.{^+}NH(CH_2CH_2OH)_3$ are used.

As the nonionic surfactant, a fatty acid diethanolamide $C_{11}H_{23}$—$CON(CH_2CH_2OH)_2$, a polyoxyethylene alkyl ether (AE) $C_{12}H_{25}$—$O(CH_2CH_2O)_8H$, and a polyoxyethylene alkyl phenyl ether (APE) $C_9H_{19}$—$(C_6H_4)O(CH_2CH_2O)_8H$ are used.

As the cationic surfactant, an alkyltrimethyl ammonium salt $C_{12}H_{25}$—$N^+(CH_3)_3.Cl^-$, a dialkyldimethyl ammonium chloride $C_{12}H_{25}$—$N^+(C_8H_{17})(CH_3)_2.Cl^-$, and an alkyl pyridinium chloride $C_{12}H_{25}$—$(N^+C_5H_5).Cl^-$ are used.

As the amphoteric surfactant, an alkyl carboxybetaine [betaine-based] $C_{12}H_{25}$—$N^+(CH_3)_2.CH_2COO^-$ is used.

The method of impregnating with a water-soluble material or a thermosoluble material will now be described.

The impregnating water-soluble material or thermosoluble material is charged in a beaker and heated to an appropriate temperature thereby reducing viscosity. A proper amount of a surfactant is added. After reducing the viscosity, a ceramic sintered body is put in the beaker, and the beaker is placed in a vacuum desiccator. The air in the vacuum desiccator is gradually extracted thereby discharging the air in the ceramic sintered body outside of the vacuum desiccator. As the evacuation progresses, air bubbles are formed on a surface of the sintered body, and thus it is found that the air in the sintered body has been extracted. After the completion of extraction of the air, impregnation is conducted by gently returning the air to the desiccator.

The organic material is preferably at least one of a thermosetting resin a thermoplastic resin and a resin containing a crosslinking agent. An epoxy resin is more preferred.

The method for forming false dental caries or a false tooth pulp in the tooth for a jaw and tooth model of the present invention will now be described.

The carious dental site or tooth pulp portion is formed of a combustible thermosetting resin material. When a tooth is produced using a die, a CIM material is injection-molded so as to coat the carious dental site or tooth pulp portion formed of the combustible thermosetting resin material. Then, the carious dental site or tooth pulp portion fired to form a hollow carious dental site or tooth pulp portion.

A silicone rubber is poured into the hollow carious dental site or tooth pulp portion to form false dental caries or false tooth pulp.

A dental caries shape is formed at a portion of a fossa of an occlusal surface or an enamel-dentin transition portion. When it is formed of the portion of fossa, enamel is not drastically attacked, but the dentin portion is often drastically attacked. A method of reproducing a bag-shaped carious dental site has previous not been accomplished.

Also in the tooth pulp shape, only small pores are opened outside like the apical foramen, similarly, and a method of reproducing a bag-shaped tooth pulp site having a large tooth pulp portion therein has previous not been accomplished.

When the enamel portion of the tooth is impregnated with a resin, the carious dental portion or tooth pulp portion may be impregnated with a resin at the same time. Before the enamel portion of the tooth is impregnated with the resin, it is possible to prevent the resin from impregnating the inorganic powder sintered body at the dental caries and an inorganic powder sintered body at the tooth pulp side by impregnating the carious dental portion or tooth pulp portion with resin, the resin being previously cured by polymerization. Thus the grinding feel becomes more closely to that of a natural tooth and it is preferred.

The material used for the carious dental portion or tooth pulp portion can be freely selected from an elastic resin, a foamed resin, a thermosetting resin, a thermoplastic resin, a resin containing a crosslinking agent, a water-soluble material, and a thermosoluble material.

A foamed resin and a thermosetting resin are preferably used for the carious dental portion. A thermosetting resin or a resin containing a crosslinking agent is preferred. An epoxy resin is more preferred.

An elastic resin, a foamed resin and a thermosetting resin are preferably used for the tooth pulp.

The method of impregnating with a water-soluble material and a thermosoluble material, which can be used for the carious dental portion or tooth pulp portion, is the same as described above.

Any silicone rubber can be used in the carious dental portion or tooth pulp portion in the ceramics sintered body of the tooth for a jaw and tooth model of the present invention without any limitation. It is particularly preferred to apply to the tooth pulp portion. Examples of the other usable rubber material include a chlorosulfonated polyethylene rubber; a Hypalon rubber, a fluororubber and an isobutene-isoprene rubber; a butyl rubber, a natural rubber and an acrylonitrile-butadiene rubber: a Hiker rubber, a urethane rubber, an ethylene-propylene rubber, a styrene-butadiene rubber and a chloroprene rubber; and neoprene. The rubber hardness (Durometer (JIS K 6253)) is from 10 to 70, and preferably from 20 to 50.

As the wax of the carious dental portion or tooth pulp portion in ceramics sintered body of the tooth for a jaw and tooth model of the present invention, for example, animal-derived wax (beeswax, spermaceti, shellac wax, etc.), plant-derived wax (Carnauba wax, Japan tallow, rice bran wax (rice wax), Candelilla wax, etc.), petroleum-derived wax (paraffin wax, microcrystalline wax, etc.), mineral-derived wax (Montan wax, ozocerite, etc.), synthetic wax (Fischer-Tropsch wax, polyethylene wax, fats and oils-based synthetic wax (ester, ketones, amides), and hydrogenated wax can be used. It is particularly preferred to apply to the tooth pulp portion. Among these waxes, petroleum-derived wax is preferred and paraffin wax is particularly preferred.

The water-soluble material of the carious dental portion or tooth pulp portion in the ceramics sintered body of the tooth for a jaw and tooth model of the present invention contains at least one of polysaccharides and protein-based material. The water-soluble material can exert the effect by water pouring or previously impregnating water. A protein is preferred.

A hydrophilic polymer is also preferably used as the water-soluble material. For example, cellulose derivatives such as natural product-derived semisynthetic carboxymethyl cellulose (CMC) and methyl cellulose (MC); and synthetic water-soluble polymers such as polyvinyl alcohol (PVA), a polyacryl-based polymer, polyacrylamide (PAM) and polyethylene oxide (PEO) can be used.

The combustible material is not specifically limited as long as it can be formed into a tooth pulp shape and is not deformed at the injection pressure and temperature upon formation of a tooth, and is also combusted upon firing of the tooth to form a tooth pulp space. Specifically, it is a resin and is particularly preferably a thermosetting resin. Specifically, it may be obtained by crosslinking a urea resin, a melamine resin, a phenol resin, an epoxy resin, an acryl-based resin or a styrene-based resin.

The combustible tooth pulp forming step of forming a combustible material tooth pulp formed at a carious dental portion or a tooth pulp portion using a combustible material is the step of previously forming a carious dental portion or a tooth pulp portion using a combustible material upon firing of a tooth so as to form a tooth pulp shape of the tooth.

Since the tooth formed of an inorganic material is subjected to the firing step, the combustible material is fired to form a space and then the space is filled with a material suited for a tooth pulp to complete a tooth. This step is the tooth pulp shape forming step.

The die setting step of setting a carious dental portion or tooth pulp portion formed of a combustible material at a predetermined position in a tooth die is the step of setting a carious dental portion or tooth pulp portion formed of a combustible material in a die. A carious dental portion or tooth pulp portion formed previously of a combustible material may be set in a die, or a carious dental portion or tooth pulp portion formed continuously in-situ of a combustible material may be set in a die again.

The injecting step of injecting pellets comprising an inorganic powder and a binder into a tooth die to obtain an inject-molded tooth is a step in which pellets are injected, the pellets obtained by mixing an inorganic powder comprising a dental composition with a binder with heating in a tooth die with a carious dental portion or tooth pulp portion formed of a combustible material. In this step, since the carious dental portion or tooth pulp portion formed of the combustible material is thin, injection must be conducted while paying careful attention.

The firing step of firing an inject-molded tooth after greasing to obtain a fired tooth is a step in which the inject-molded tooth obtained in the injecting step is fired. The firing temperature in the firing step is from 800 to 1200° C. when a large amount of a glass component is contained. In case of alumina, the firing temperature is from 1,200 to 1,600° C., and preferably from 1,400 to 1,550° C. At this time, carious dental portion or tooth pulp portion formed of the combustible material is burned out to form a space portion.

The tooth pulp production method of filling the fired carious dental portion or tooth pulp portion with a resin, a silicone rubber, a wax or a water-soluble material is the step of forming a false tooth pulp at the space portion of the fired tooth pulp using a resin, a silicone rubber, a wax or a water-soluble material. Examples of the method include a method of filling using a syringe, and a method of filling a tooth pulp portion of a sintered body with a false tooth pulp material by immersing in the false tooth pulp material and placing in a vacuum vessel, followed by evacuation.

A method for producing a tooth for a jaw and tooth model of the present invention will now be described.

EXAMPLES

Production of Sintered Body of Tooth

Sintered Body 1

A die capable of injection-molding into a tooth shape was produced. 1 kg of an alumina pellets for CIM (the content of $Al_2O_3$: 100%, average particle diameter: 5.0 μm, the content of stearic acid: 30%) as a raw material of a tooth were injection-molded in a die for tooth to obtain an injection molding 1.

The resultant injection molding having a tooth shape was degreased and then fired (1,500° C., retention time: 10 minutes) to obtain a sintered body 1.

Sintered Body 2

A die capable of injection-molding into a tooth shape was produced. 1 kg of an alumina pellets for CIM (the content of $Al_2O_3$: 100%, average particle diameter: 1.0 μm, the content of stearic acid: 30%) as a raw material of a tooth were injection-molded in a die for tooth to obtain an injection molding 2.

The resultant injection molding having a tooth shape was degreased and then fired (1,500° C., retention time: 10 minutes) to obtain a sintered body 2.

Impregnation with Resin

The crown portion of the resultant sintered bodies 1 and 2 was immersed in each material shown below and placed in a vacuum vessel, followed by evacuation. After standing for 10 minutes, the pressure was returned to a normal pressure thereby impregnating with each material to form an enamel portion (Examples 1 to 6). The impregnation depth varies depending on the particle size of an alumina powder contained in alumina pellets and an impregnating resin material, and is from 0.5 to 5.0 mm.

Thirty teeth were produced and the grinding feel of the teeth was confirmed.

Tested Resin

Epoxy resin (low viscosity epoxy resin Z-2/H-07): An epoxy resin containing a catalyst added therein was used. The pressure was returned to a normal pressure. 72 hours after standing, the grinding feel was confirmed using a diamond bar.

Acrylic resin (MMA monomer, manufactured by KURARAY CO., LTD.): An acryl-based resin containing a chemical polymerization catalyst added therein was used. The pressure was returned to a normal pressure. 72 hours after standing, the grinding feel was confirmed using a diamond bar.

Melamine resin (RTV silicone resin M8017, manufactured by Asahi Kasei Corporation): A silicone resin containing a catalyst added therein was used. The pressure was returned to a normal pressure. 72 hours after standing, the grinding feel was confirmed using a diamond bar.

As Comparative Examples, non-impregnated sintered bodies 1 and 2 (Comparative Examples 1 to 2) were used.

TABLE 1

| | Sintered body | Impregnating resin | Grinding feel | Dentin-enamel transition feel |
|---|---|---|---|---|
| Example 1 | Sintered body 1 | Epoxy resin | A | A |
| Example 2 | | Acrylic resin | A | A |
| Example 3 | | Melamine resin | A | A |
| Comparative Example 1 | | | B | C |
| Example 4 | Sintered body 2 | Epoxy resin | A | A |
| Example 5 | | Acrylic resin | A | A |
| Example 6 | | Melamine resin | A | A |
| Comparative Example 2 | | | B | C |

Evaluation Criteria
Grinding Feel
A: Grinding feel of dentin portion and enamel portion could be sufficiently exhibited.
B: Grinding feel of dentin portion and enamel portion could not be sufficiently exhibited.
Dentin-Enamel Transition Feel
A: Difference in grinding feel could be sufficiently exhibited upon transition between dentin portion and enamel portion.
B: Difference in grinding feel could not be sufficiently exhibited upon transition between dentin portion and enamel portion.
C: Difference in grinding feel could not be completely exhibited upon transition between dentin portion and enamel portion.

In Examples 1 to 6, it was possible to obtain a grinding feel which is tough when compared with Comparative Examples 1 and 2 and is similar to that of a natural tooth. Crushing feel peculiar to ceramics upon grinding was scarcely confirmed and the feel closed to feel upon grinding of the living body tooth.

It was possible to obtain a tooth comprising an enamel portion and a dentin portion, each having different grinding feel, similarly to a natural tooth by controlling the evacuation amount, evacuation time and immersion time thereby adjusting the resin impregnation depth.

When dentin and enamel are separately formed, since chipping occurred between the dentin and enamel, training related to tooth grinding could not be easily conducted.

Impregnation with Glass

A paste prepared from each material shown below was built up on a crown portion of the resultant sintered bodies 1 and 2 and then fired at each temperature shown below thereby impregnating with each material to form an enamel portion (Examples 7 to 10). The impregnation depth varies depending on the particle size of an alumina powder contained in alumina pellets and an impregnating glass material, and is from 0.5 to 5.0 mm.

Thirty teeth were produced and grinding feel of the teeth.
Tested Glass
$PbO$—$SiO_2$—$B_2O_3$: firing temperature of 550° C.
Alumina silicate glass: firing temperature of 950° C.

TABLE 2

|  | Sintered body | Impregnating glass | Grinding feel | Dentin-enamel transition feel |
|---|---|---|---|---|
| Example 7 | Sintered body 1 | $PbO$—$SiO_2$—$B_2O_3$ | A | A |
| Example 8 |  | Alumina silicate glass | A | A |
| Example 9 | Sintered body 2 | $PbO$—$SiO_2$—$B_2O_3$ | A | A |
| Example 10 |  | Alumina silicate glass | A | A |

Evaluation Criteria
Grinding Feel
A: Grinding feel of dentin portion and enamel portion could be sufficiently exhibited.
B: Grinding feel of dentin portion and enamel portion could not be sufficiently exhibited.
Dentin-Enamel Transition Feel
A: Difference in grinding feel could be sufficiently exhibited upon transition between dentin portion and enamel portion.
B: Difference in grinding feel could not be sufficiently exhibited upon transition between dentin portion and enamel portion.
C: Difference in grinding feel could not be completely exhibited upon transition between dentin portion and enamel portion.

In Examples 7 to 8, it was possible to obtain grinding feel which is tough and is similar to that of a natural tooth. Crushing feel peculiar to ceramics upon grinding was scarcely confirmed and the feel was close to the feel upon grinding of the living body tooth.

It was possible to obtain a tooth comprising an enamel portion and a dentin portion, each having a different grinding feel, similarly to a natural tooth by controlling the kind of glass and firing time after building up of the glass thereby adjusting the low melting point glass impregnation depth.

The resultant tooth can be used as a tooth for training related to grinding of a natural tooth in universities for dentist training.

What is claimed is:

1. A tooth for a jaw and tooth model, which is used for training related to a treatment, the tooth comprising an enamel portion and a dentin portion,
   wherein the enamel portion and the dentin portion comprise an integrally formed sintered body of an inorganic powder, the sintered body having voids existing between sintered inorganic powder particles of the sintered body, and
   wherein only the voids in the enamel portion are impregnated with a resin or a low melting point glass so that the enamel portion is harder than the dentin portion.

2. The tooth for a jaw and tooth model according to claim 1, wherein the inorganic powder is selected from the group consisting of alumina-based, zirconia-based, silica-based, titanium oxide-based, aluminum nitride and silicon nitride ceramic powders.

3. The tooth for a jaw and tooth model according to claim 1, wherein the resin or low melting point glass is a thermosetting resin.

4. The tooth for a jaw and tooth model according to claim 1, wherein the resin or low melting point glass is a low melting point glass which flows at a temperature within a range from 200 to 600° C.

5. The tooth for a jaw and tooth model according to claim 1 wherein a tooth pulp portion is formed in the dentin portion.

6. The tooth for a jaw and tooth model according to claim 5 wherein the tooth pulp portion contains a resin, a silicone rubber, a wax or a water-soluble material.

7. The tooth for a jaw and tooth model according to claim 1, which comprises a false carious dental portion between the enamel portion and the dentin portion, or at the periphery thereof, or the dentin side in the vicinity of a transition portion of the enamel portion and the dentin portion.

8. The tooth for a jaw and tooth model according to claim 1, wherein the resin or low melting point glass is a thermosetting resin.

9. The tooth for a jaw and tooth model according to claim 2, wherein the resin or low melting point glass is a thermosetting resin.

10. The tooth for a jaw and tooth model according to claim 1, wherein the resin or low melting point glass is a low melting point glass which flows at a temperature within a range from 200 to 600° C.

11. The tooth for a jaw and tooth model according to claim 2, wherein the resin or low melting point glass is a low melting point glass which flows at a temperature within a range from 200 to 600° C.

12. A tooth for a jaw and tooth model for use in training related to a treatment, the tooth being formed by a process comprising the steps of:
   integrally molding an enamel portion and a dentin portion from a pellet comprising an inorganic powder and a binder, the inorganic powder having a particle size in a range of 0.1 to 10 μm;
   heating the integrally molded enamel portion and dentin portion to remove the binder;
   firing the integrally molded enamel portion and dentin portion to form a sintered body; and
   impregnating only a part of the sintered body corresponding to the enamel portion with a resin or a low melting point glass so that the resin portion is harder than the dentin portion.

* * * * *